United States Patent [19]
Hoffman et al.

[11] Patent Number: 6,066,623
[45] Date of Patent: *May 23, 2000

[54] POLYNUCLEOTIDE VACCINE PROTECTIVE AGAINST MALARIA, METHODS OF PROTECTION AND VECTOR FOR DELIVERING POLYNUCLEOTIDE VACCINES

[75] Inventors: Stephen L. Hoffman; Richard C. Hedstrom; Martha Sedegah, all of Gaithersburg, Md.

[73] Assignee: The United States of America as represented by the Secretary of the Navy, Washington, D.C.

[ * ] Notice: This patent is subject to a terminal disclaimer.

[21] Appl. No.: 08/155,888

[22] Filed: Nov. 23, 1993

[51] Int. Cl.$^7$ .............................. A61K 48/00; C12N 5/00; C12N 15/00
[52] U.S. Cl. .......................... 514/44; 514/895; 435/320.1; 935/65
[58] Field of Search ................................ 424/88; 514/14, 514/895; 435/320.1; 935/65

[56] References Cited

PUBLICATIONS

Bryan Rd. Cullen, Cell, vol. 46, pp. 973–982, Sep. 26, 1986.
Hoffman et al., Preerythrocytic Malaria Vaccine Development*, Job PACKBJ 5258$$$$28 Galley—05–07–93 08–07–01.
Ulmer et al., Science, vol. 259, pp.1745–1749, Mar. 19, 1993.
Robinson et al (1992) Modern Approaches to Vaccines, Including Prevention of Aids, Cold Spring Harbor, 92.
Caspers et al (1989) Molec. Biochem Paraset. 35, 185–190.
Lal et al (1987) J. Biol. Chem. 262, 2937–2940.
Good et al (1987) Nature 235, 1059–1062.
Ostro et al (1989) Am. J. Hospt. Pharm. 46, 1576–1587.
Arnott et al(1985) Science 230, 815–818.
Wolff et al (1990) Science 247, 1465–1468.
Lal et al (1988) Molec. Biochem. Parasit. 30, 291–294.
Fasel et al (1992) Gene 111, 157–163.
Young et al (1985) Science 228, 958–962.
Caspeb et al (1989) Molec. Biochem. Parasit. 35, 185–190.

*Primary Examiner*—Deborah Crouch
*Attorney, Agent, or Firm*—A. D. Spevack

[57] ABSTRACT

A first embodiment is a specific plasmid vector, pDIP/PyCSP.1, into which nucleotides encoding the targets of specific immune responses are inserted. These targets include, but are not limited to proteins and peptides. These plasmid constructs are incorporated in a composition comprising a suitable and acceptable art recognized pharmaceutical reagent that is benign (non-reactive with) to the plasmid construct. The plasmid construct provides protective immune responses to the disease associated with the selected targets. A second embodiment is a construct having, at a minimum, the nucleotide sequences encoding one or more Plasmodium species proteins in a pharmaceutically acceptable vector. a third embodiment is a method of controlling malaria in mammals comprising injecting a polynucleotide delivery vector into a mammal.

8 Claims, 7 Drawing Sheets

POLYNUCLEOTIDE VACCINE PROTECTIVE AGAINST MALARIA, METHODS OF PROTECTION AND VECTOR FOR DELIVERING POLYNUCLEOTIDE VACCINES

BACKGROUND OF THE INVENTION

1. Field of the Invention

This invention relates to polynucleotide vaccines protective against malaria, and a vector for construction of this and other polynucleotide vaccines. More particularly, this invention relates to vaccines composed of, at a minimum, nucleotides encoding one or more Plasmodium species proteins, and compositions and methods of providing protection against malaria with such a polynucleotide vaccine. Also, the invention includes a plasmid vector including a cytomegalovirus promotor for insertion of nucleotides encoding targets of protective immune responses.

2. Description of the Prior Art

There have been major efforts toward development of malaria vaccines undertaken during the past 20 years. Although a commercially viable vaccine has not been achieved to the time this application is filed, there have been successes in providing vaccine protection. The continued vast investment in vaccine research by both governments world wide and industry shows an expectation of achieving a commercially viable vaccine. A commercially viable vaccine is one that provides protection with minimum side effects, is capable of being produced in quantity, and is stable in storage for a reasonable time under reasonable conditions. These conditions and requirements are well known in the medical and pharmaceutical arts. Even the near misses of total successes (e.g. successes with only a small population) are useful in understanding the mechanisms of malaria and further defining the parameters that will lead to a commercially successful vaccine or treatment. The current status of malaria vaccine development has been summarized in a recent Institute of Medicine Report[1]. The introduction to the section on vaccines is included verbatim to provide part of the background for this application.

Where We Are Today

Prospects for a Vaccine

Vaccination is an exceptionally attractive strategy for preventing and controlling malaria. Clinical and experimental data support the feasibility of developing effective malaria vaccines. For example, experimental vaccination with irradiated sporozoites can protect humans against malaria, suggesting that immunization with appropriate sporozoite and liver-stage antigens can prevent infection in individuals bitten by malaria-infected mosquitoes. In addition, repeated natural infections with the malaria parasite induce immune responses that can prevent disease and death in infected individuals, and the administration of serum antibodies obtained from repeatedly infected adults can control malaria infections in children who have not yet acquired protective immunity. These data suggest that immunization with appropriate blood-stage antigens can drastically reduce the consequences of malaria infection. Finally, experimental evidence shows that immunization with sexual-stage antigens can generate an immune response that prevents parasite development in the vector or, offering a strategy for interrupting malaria transmission.

Prospects for the development of malaria vaccines are enhanced by the availability of suitable methods for evaluating candidate antigens. These include protocols that allow human volunteers to be safely infected with malaria, and the identification of many areas in the world where more than 75 percent of individuals can be expected to become infected with malaria during a three-month period. In contrast to vaccines for diseases of low incidence, for which tens of thousands of immunized and nonimmunized controls must be studied over several years, malaria vaccines could be evaluated in selected areas in fewer than 200 volunteers in less than a year.

Developments in molecular and cellular biology, peptide chemistry, and immunology provide the technological base for engineering subunit vaccines composed of different parts of the malaria parasite, an approach that was not possible 10 years ago. During the past 5 years, more than 15 experimental malaria vaccines have undergone preliminary testing in human volunteers. Although none of these vaccines has proven suitable for clinical implementation, progress has been made in defining the parameters of a successful vaccine and the stage has been set for further advancement.

Despite the inherent attractiveness and promise of this approach, there remain a number of obstacles to vaccine development. With the exception of the erythrocytic (blood) stages of P. falciparum, human malaria parasites cannot be readily cultured in vitro, limiting the ability of researchers to study other stages of this parasite and all stages of the other three human malaria parasite species.

In vitro assays, potentially useful for screening candidate vaccines for effectiveness, do not consistently predict the level of protective immunity seen in vivo. The only laboratory animals that can be infected with human malaria parasites are certain species of nonhuman primates, which are not naturally susceptible to these organisms. This makes it difficult to compare the results of many studies done in animals with what happens in human malaria infection.

The promises of modern vaccinology, while potentially revolutionary, have so far proved elusive. Few commercially available vaccines have been produced by this technology, for both scientific and economic reasons. Scientists have not yet been able to assemble defined synthetic peptides and recombinant proteins and combine them with new adjuvants and delivery systems into a practical human malaria vaccine. However, as discussed above and in the remainder of this chapter, there are good reasons to believe that this approach will ultimately succeed.

Approaches to Vaccine Development

The complex life cycle of the malaria parasite provides a number of potential targets for vaccination. Under investigation are vaccines that would be effective against the extracellular sporozoite, during the short period it spends in the bloodstream; the exoerythrocytic (or liver-stage) parasite, during the roughly seven days it develops within liver cells; the extracellular merozoite, released from liver cells or infected erythrocytes and free in the circulation prior to invading other erythrocytes; the asexual parasite that develops within red blood cells; exogenous parasite material released from infected erythrocytes; and the sexual-stage parasite, which occurs both inside erythrocytes and in mosquitoes. The optimal vaccine would include antigens from the sporozoite, asexual, and sexual stages of the parasite, thus providing multiple levels of control, but vaccines effective against individual stages could also prove highly useful. In addition, a vaccine against the Anopheles mosquito itself, which reduced the insect's life span and prevented complete development of the parasite, could be valuable.

Regardless of the stage of parasite targeted for vaccine development, a similar strategy is envisioned. Based on knowledge of the mechanisms of protective immunity, specific parasite antigens (immunogens) are identified that induce a protective immune response, and synthetic or recombinant vaccines that accurately mimic the structure of that antigen are prepared.

In the subunit approach to vaccine development, this is done by combining the immunogen with carrier proteins, adjuvants, and live vectors or other delivery systems. This approach is being pursued throughout the world in laboratories studying infectious diseases. Clinical utility has yet to be demonstrated for the majority of these efforts, and barriers to obtaining satisfactory immunization by the subunit approach remain. Nevertheless, research on malaria subunit vaccines will continue to be at the cutting edge of this innovative and important approach to vaccine development.

It is clear from this description that major advances have been made, and many parasite proteins that could be targets of vaccine development have been identified. What has been lacking is an effective, economically feasible method for inducing protective immune responses against these already identified proteins. Perhaps the most striking example has been in the field of pre-erythrocytic stage malaria vaccine development in which there is already an effective vaccine for humans, the irradiated sporozoite vaccine, but the vaccine is totally impractical for widespread human use because of production and administration problems.

The Irradiated Sporozoite Model

In the 1940s, Mulligan and colleagues[2] demonstrated that immunization of chickens with radiation attenuated *Plasmodium gallinaceum* sporozoites induced protective immunity. In the late 1960s, Nussenzweig and colleagues[3] demonstrated that immunization of A/J mice with radiation attenuated *P. berghei* sporozoites protected mice against challenge with live sporozoites. This immunity was stage specific; mice challenged with infected erythrocytes were not protected. In the early 1970s Clyde and colleagues[4-6] and Rieckmann and colleagues[7,8] demonstrated that immunization of humans by the bite of irradiated Anopheles species mosquitoes carrying *P. falciparum* and in one case *P. vivax* sporozoites in their salivary glands protected these volunteers against challenge with live sporozoites. Like the immunity in mice, this immunity was stage specific, and it was also species specific; immunization with *P. falciparum* did not protect against *P. vivax*. However, it was not strain specific; immunization with *P. falciparum* sporozoites from Burma protected against challenge with sporozoites from Malaya, Panama and the Philippines[4], and immunization with sporozoites from Ethiopia protected against challenge with a strain from Vietnam[8]. These human studies have been repeated recently[9,10] reconfirming that there already is an effective malaria vaccine, and demonstrating this protective immunity lasts for at least 9 months[11]. Unfortunately, sporozoites have to be delivered alive, and since mature, infective sporozoites have never been produced in vitro, and it is impractical to immunize large number of individuals by the bite of thousands of sporozoite-infected mosquitoes, the targets and mechanisms of this protective immune response had to be identified so as to construct a synthetic or recombinant vaccine.

Radiation attenuated sporozoites develop only to late trophozoites in the liver, and this observation and the finding that irradiated sporozoite induced immunity does not protect against challenge with infected erythrocytes, indicate that the immunity is directed against the sporozoite as it rapidly makes its way from inoculation by the mosquito to the hepatocytes, or against the infected hepatocyte. Since the sporozoite is primarily extracellular during the 60 minutes or less that it takes to invade hepatocytes,[12] antibodies may prevent sporozoites from effectively invading hepatocytes, and either antibodies or T cells could recognize parasite antigens expressed in infected hepatocytes, and destroy these cells. Initial efforts to develop pre-erythrocytic malaria vaccines focused on producing protective antibodies. Currently there is increasing recognition of the requirement to attack the infected hepatocyte, primarily through T cell mediated mechanisms.

The circumsporozoite protein (CSP) is a target of this pre-erythocytic immunity[13]. In the *Plasmodium yoelii* (Py) rodent model system passive transfer of Mabs against the PyCSP[14], and adoptive transfer of CD8+ [15,16] and CD4+ [17] T cell clones against the PyCSP are protective. Numerous vaccines designed to protect mice against sporozoites by inducing immune responses against the PyCSP have been evaluated. They have often induced antibodies and cytotoxic T lymphocytes (CTL) with the specificities of the protective Mabs and T cell clones, and partial protection[18-22] but none have induced levels of protective immunity comparable to that found after immunization with radiation attenuated sporozoites, or transfer of Mabs or T cell clones.

It has recently been shown that immunization with naked DNA by biolistic[23] and intramuscular (IM) routes induces antibodies against foreign proteins[24,25], and in one study in mice, CTL and protection against influenza virus[26]. The literature is silent on the applicability of naked DNA immunization to prevent malaria, and to specific plasmid vectors shown to be useful for inserting the genes encoding Plasmodium species proteins for protection against malaria that could be used to prevent other diseases.

SUMMARY OF THE INVENTION

Accordingly, an object of this invention is to protect a subject or community against malaria caused by Plasmodium species parasites.

Another object of this invention is to provide protection using a vaccine that does not rely on live recombinant vectors, synthetic peptides, or purified recombinant proteins.

A further object of this invention is to protect against malaria by immunization with a vaccine that induces protective immune responses against one or more Plasmodium parasite proteins.

Yet another object of this invention is a vaccine composed of nucleotides effective to protect against infection with Plasmodium species and/or to prevent malaria.

Yet an additional object of this invention is a plasmid vector that can be used to construct polynucleotide vaccines for induction of protective immune responses.

These and additional objects of the invention are accomplished by a first embodiment of a specific plasmid vector, pDIP/PyCSP.1, into which nucleotides encoding the targets of specific immune responses are inserted. These targets include, but are not limited to proteins and peptides. These plasmid constructs are incorporated in a composition comprising a suitable and acceptable art recognized pharmaceutical reagent that is benign (non-reactive with) to the plasmid construct. The plasmid construct is utilized by injection (intramuscular, intravenous, intradermal, subcutaneous), inhalation, topical application, or ingestion of the DNA into humans to induce protective immune responses to the disease associated with the selected targets. The specific doses to be delivered are determined after studies of safety, toxicity, and immunogenicity so as to induce the best immune responses without placing the patient at increased risk and without inducing unacceptable side effects. The methods for identifying appropriate doses are well known in the art.

A second and preferred embodiment is a construct having at a minimum the nucleotide sequences encoding one or more Plasmodium species proteins as illustrated in cartoon form in FIG. 1. An example would be pDip/PfCSP into which the gene encoding the *Plasmodium falciparum* circumsporozoite protein (CSP) has been inserted. FIG. 1 also shows that polynucleotides encoding Plasmodium sp. proteins could be inserted into any vector (circular or linear) so as to induce immune responses against these proteins, or that the polynucleotides could be injected without insertion into a vector. These constructs are applied by incorporation into an injectable, an inhalant, a topically applied substance or an ingestible substance comprising a suitable and acceptable art recognized pharmaceutical reagent. These preparations are used in mammals including humans to produce protective immune responses against Plasmodium.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

FIGS. 6A & 6B are a pair of graphs that compare the cytolytic activity against PyCSP after immunization with pDIP/PyCSP.1 and irradiated sporozoites wherein:

FIG. 6A is a graph of results of mice immunized with 3 doses of pDIP/PyCSP.1

FIG. 6B is a graph of results of mice immunized with 3 doses of irradiated *P. yoelii* sporozoites.

DESCRIPTION OF THE PREFERRED EMBODIMENTS

Figure 3:
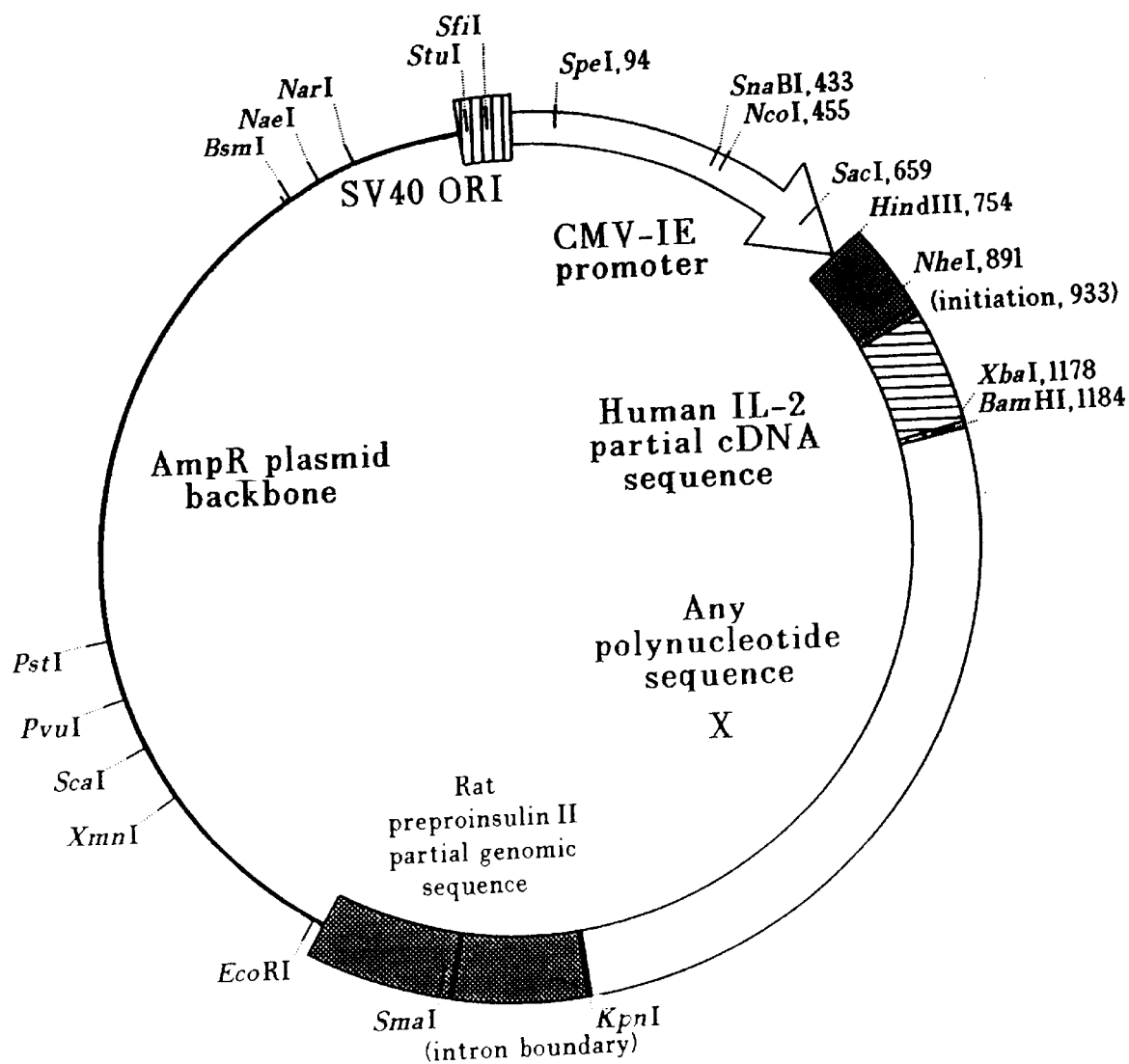
FIG. 3 is a physical map of a hypothetical plasmid vector pDIP/X

In the first embodiment, a plasmid vector was constructed for use in the delivery in vivo of polynucleotides (cDNA, DNA, RNA,) the sequences of which encode the synthesis of molecules that provide beneficial therapeutic or immunological (protective) responses in mammalian subjects. In research results published by Cullen[27], the plasmid vector pBC12/CMV/IL-2 when transfected in vitro into mammalian tissue culture cells effectively utilized the cytomegalovirus (CMV) promoter of transcription to drive expression of human interleukin 2 (IL-2). These results suggested a rationale for a plasmid based on Cullen's plasmid vector that could be used in vivo (contrary to Cullen's vector that included the intact IL2) to express any polynucleotide sequence from inside mammalian cells following delivery of the plasmid by injection (intramuscular, subcutaneous, intradermal, intravenous), inhalation, topical application, or ingestion into the body of a mammalian subject. This vector leads to the expression of polynucleotides encoding the first six amino acids of the rat preproinsulin signal peptide, the first 82 amino acids of the human IL-2 protein, and the targets in parasites, viruses, bacteria, fungi, toxins, and other molecules of mammalian protective immune responses. Depicted in FIG. 3, pDIP/X is an illustration of a derived construct of pDIP/PyCSP.1 in which any polynucleotide X (cDNA, DNA, RNA) is inserted downstream of the CMV promoter using for example one or more combinations of the following restriction endonucleases to modify the parent pDIP/PyCSP.1 plasmid for other uses: HindIII, NheI, XbaI, BamHI, HincII, KpnI, SmaI, EcoRI, or any endonucleases that recognize sites within the PyCSP gene sequence (not shown). The resultant plasmid from any modification of pDIP/PyCSP.1 in which polynucleotide sequences are inserted downstream of the CMV promoter will be capable of being expressed in mammalian cells and therefore the plasmid used as a vaccine, as we have shown in malaria studies with mice, or in any case where this plasmid vector is used to deliver polynucleotide sequences for expression in mammalian subjects that will have beneficial therapeutic or immunological effects.

Figure 1:
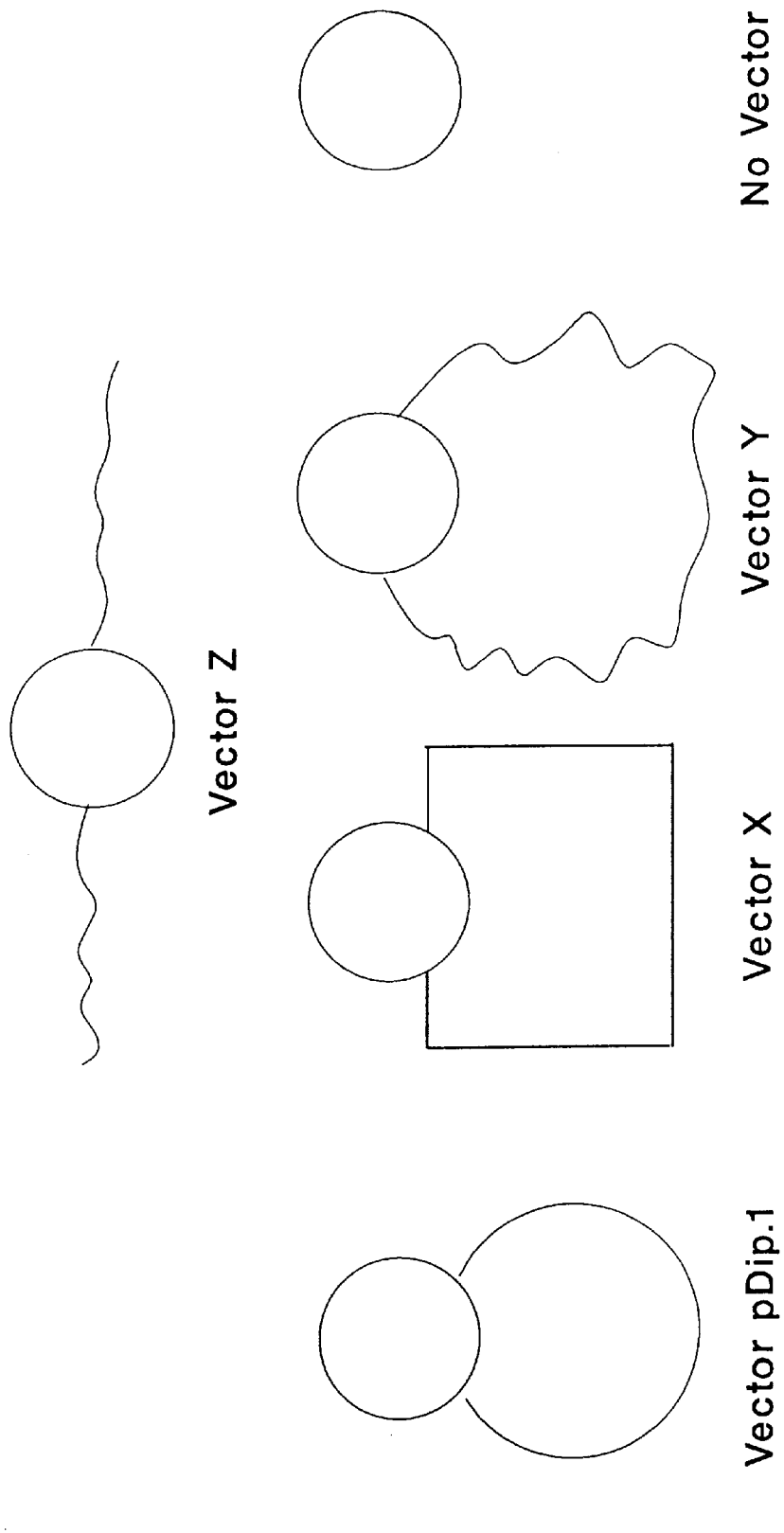
FIG. 1 of embodiments of the invention applied to Plasmodium species.

In the second embodiment, we have found that intramuscular injection with a plasmid containing polynucleotides encoding a specific protein of the Plasmodium species induces antibodies and CTL against the specific protein, and protection against challenge with the malaria parasite. Nucleotides encoding any Plasmodium sp. proteins capable of inducing protection against malaria usable in this invention can be included. Specific proteins include the known *P. falciparum, P. vivax, P. malariae,* and *P. ovale* CSP; SSP2 (TRAP); Pfs16 (Sheba); LSA-1; LSA-2; LSA-3; MSA-1 (PMMSA, PSA, p185, p190); MSA-2 (Gymmnsa, gp56, 38–45 kDa antigen); RESA (Pf155); EBA-175; AMA-1 (Pf83); SERA (p113, p126, SERP, Pf140); RAP-1; RAP-2; RhopH3; PfHRP-II; Pf55; Pf35; GBP (96-R); ABRA (p101); Exp-1 (CRA, Ag5.1); Aldolase; Duffy binding protein of *P. vivax;* Reticulocyte binding proteins; HSP70-1 (p75); Pfg25; Pfg28; Pfg48/45; and Pfg230, and the nucleotides encoding the analogues of these proteins in the other species when not yet defined. Specifically we have found that IM injection of BALB/c mice with PyCSP DNA induces antibodies and CTL against the protein, and protects against challenge with the protozoan parasite, *P. yoelii.* Polynucleotide sequences encoding one or any of the above proteins is ligated into the pDIP/PyCSP.1 plasmid or any other vector as depicted in FIG. 1.

It is believed that protection can be improved by altering immunization regimens, or immunizing with several genes or short portions of genes encoding protective B and T cell epitopes; to determine the mechanisms by which DNA immunization induces protective antibody and T cell responses; to establish the safety of this method of immunization; and to establish similar immunogenicity in non-human primates.

Having described the invention, the following examples are given to illustrate specific applications of the invention including the best mode now known to perform the invention. These specific examples are not intended to limit the scope of the invention described in this application.

EXAMPLE 1

Figure 2:
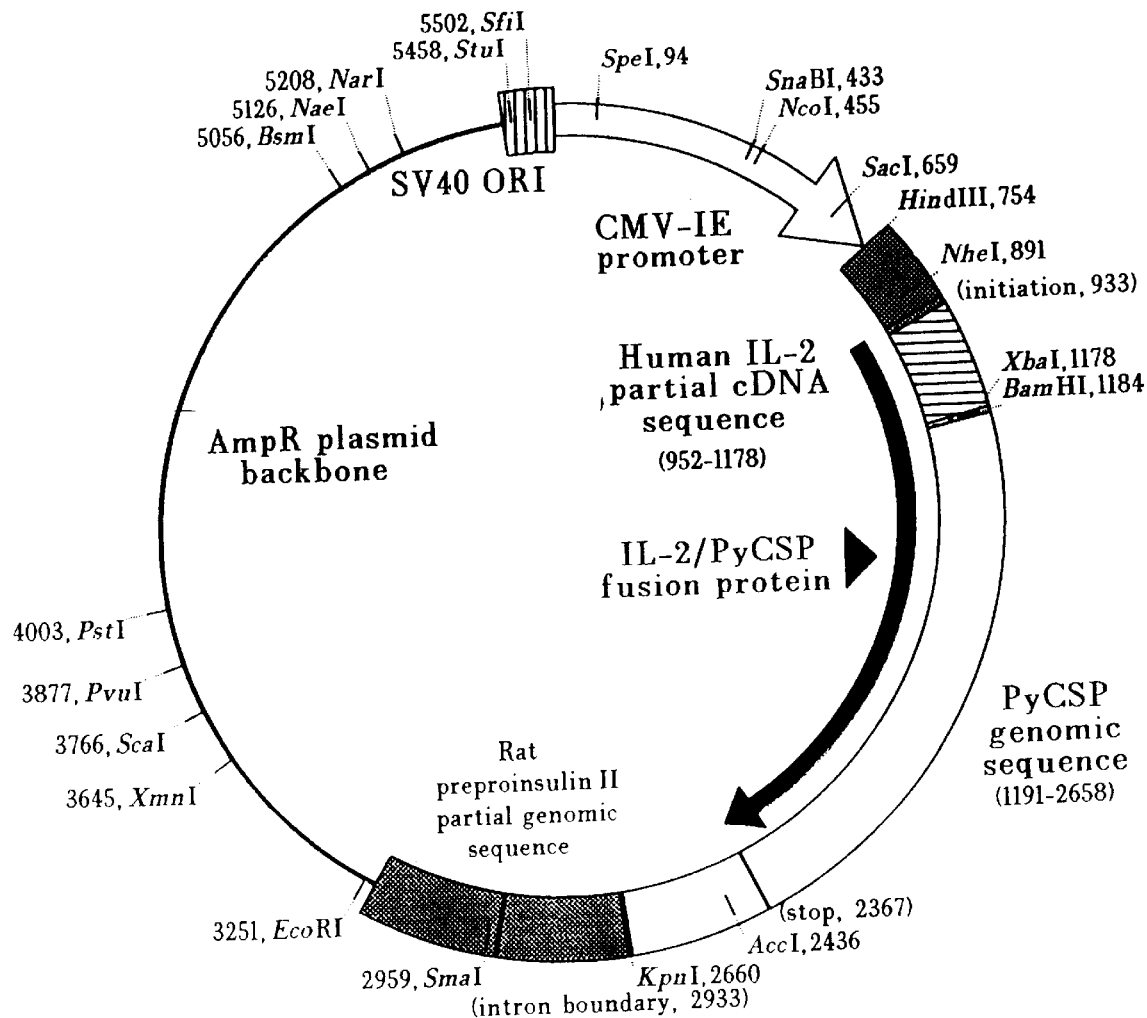
FIG. 2 is a physical map of pDIP/PyCSP.1

Our initial attempts to induce antibodies, CTL, or protective immunity by immunizing BALB/c mice by the intravenous (IV) route with a plasmid containing the entire coding region of Py sporozoite surface protein 2 (PySSP2)[28,29] in expression vector pcEXV-3 [30] were unsuccessful. Because of the success of DNA immunization with vectors containing cytomegalovirus (CMV) promoters[26], we cloned the entire coding region of PyCSP[31] into a CMV promoter vector[27] that we modified to accommodate the PyCSP gene to form pDIP/PyCSP.1 (FIG. 2).

The PyCSP gene was obtained from plasmid B155[32] as a 1468 bp Dra1/EcoRV fragment. This fragment was ligated into pUC18, which was previously digested with Sma1 followed by calf intestinal alkaline phosphatase, to form pUC18/PyCSP. A 1486bp Xbal/Kpl fragment encompassing the PyCSP gene was excised from pUC18/PyCSP and used to replace the 666 bp Xbal/Kpnl fragment of the expression vector pBC12/CMV/IL-2[27] to form pDIP/PyCSP.1.

DNA sequencing of the Xbal junction of pDIP/PyCSP.1 predicted that the entire CSP coding region was fused in-frame with the sequence encoding the first 82 amino acids of IL-2. The sequence of pDIP/PyCSP.1 plasmid is shown in Sequence ID No. 1. Sequence ID No. 2 is the translated peptides. Plasmid DNA for injections was purified by cesium chloride gradient centrifugation, sterilized by ethanol precipitation, and dissolved in sterile PBS.

Mice were injected IM in each thigh with 100 mcg of plasmid DNA dissolved in PBS with or without Lipofectin® reagent (BRL). Initial experiments indicated that delivery with Lipofectin® reagent did not augment antibody responses as measured in an indirect fluorescent antibody test (IFAT) against sporozoites (data not shown). Therefore, in subsequent experiments, plasmid DNA was delivered IM in PBS alone.

Negative control mice were injected with unmodified plasmid DNA lacking the PyCSP gene. In initial experiments antibody responses were inconsistent. After 3 doses only 9 of 13 mice had antibodies to sporozoites, and 7 of the 9 had low levels of antibodies. However, after the fourth immunization 12 of the 13 mice had moderate to high antibody titers against sporozoites (data not shown). After experience was gained with injections, and the caliber of the needle reduced from 26 gauge to 30 gauge, the frequency of antibody response improved (Table 1).

TABLE 1

Antibodies against sporozoites. Mice were immunized with pDIP/PyCSP.1 at 0 and 8 weeks, or at 0, 5 and 8 weeks. Sera were tested for antibodies to air-dried sporozoites by IFAT (7) 5, 8 and 10 weeks after the first immunization. Control mice received the pBC12/CMV/IL-2 plasmid (16, 17) without the PyCSP insert. Pooled sera taken 2 weeks after the third immunization with P. yoelii IrrSpz (7), and tested at the same time had an IFAT titer of 1280.

| Mouse | Immunizations | IFAT TITERS Weeks after first immunization | | |
|---|---|---|---|---|
| | | 5 | 8 | 10 |
| 1A | 0, 8 weeks | 40 | 40 | 20,480 |
| 2A | 0, 8 weeks | 320 | 160 | 20,480 |
| 3A | 0, 8 weeks | 320 | 160 | 20,480 |
| 7A | 0, 8 weeks | 160 | 320 | 20,480 |
| 5A | 0, 8 weeks | <10 | <10 | 10,240 |
| 6A | 0, 8 weeks | 320 | 320 | 2,560 |
| 4A | 0, 8 weeks | 80 | 80 | 2,560 |
| 3B | 0, 5, 8 weeks | 640 | 20,480 | 20,480 |
| 4B | 0, 5, 8 weeks | 640 | 10,240 | 20,480 |
| 5B | 0, 5, 8 weeks | 160 | 2,560 | 20,480 |
| 1B | 0, 5, 8 weeks | 320 | 5,120 | 5,120 |
| 2B | 0, 5, 8 weeks | 160 | 2,560 | 2,560 |
| 6B | 0, 5, 8 weeks | 160 | 2,560 | 2,560 |
| controls (n = 6) | 0, 8 weeks | <10 | <10 | <10 |
| controls (n = 6) | 0, 5, 8 weeks | <10 | <10 | <10 |

Data also indicated that delay in delivery of the second dose improved the response to 2 doses (Table 1). Antibodies in sera from mice immunized with pDIP/PyCSP.1 recognized purified recombinant P. yoelii CSP (FIG. 4).

Figure 4:
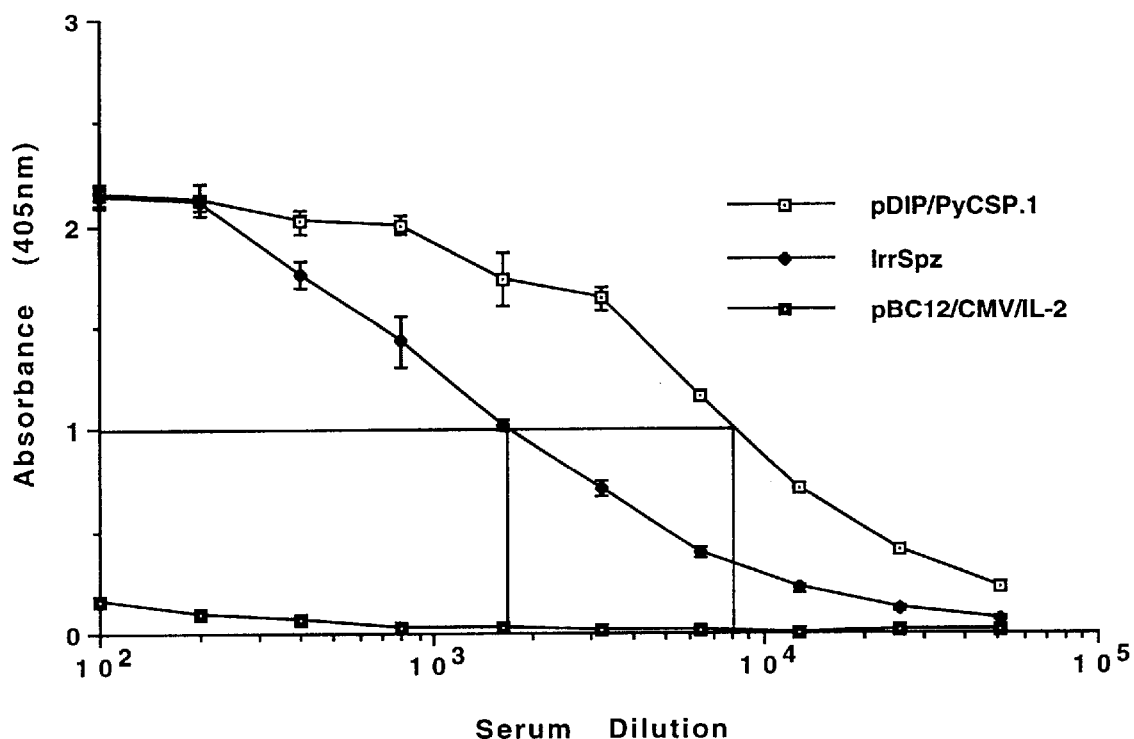
FIG. 4 is a graph that shows antibodies against a recombinant protein (PyCS.1, amino acids 64–321 of the *P. yoelii* CSP) of the *P. yoelii* CSP induced by immunization with 3 different vaccines.

The results shown in FIG. 4 were obtained from pooled sera taken from 3 mice 2 weeks after the third dose where the mice were respectively immunized with the pDIP/PyCSP.1 vaccine, irradiated P. yoelii sporozoites (IrrSpz), and plasmid control. The sera of each was assessed by ELISA as described[14] for antibodies to a recombinant fusion protein, PY CS.1, including amino acids 64 to 321 of the PyCSP. The serum dilution at which the absorbance (405 nm) was 1.0 by ELISA was 7.4 times higher in mice immunized with pDIP/PyCSP.1 as compared to those immunized with irradiated sporozoites (FIG. 4).

Figure 5:
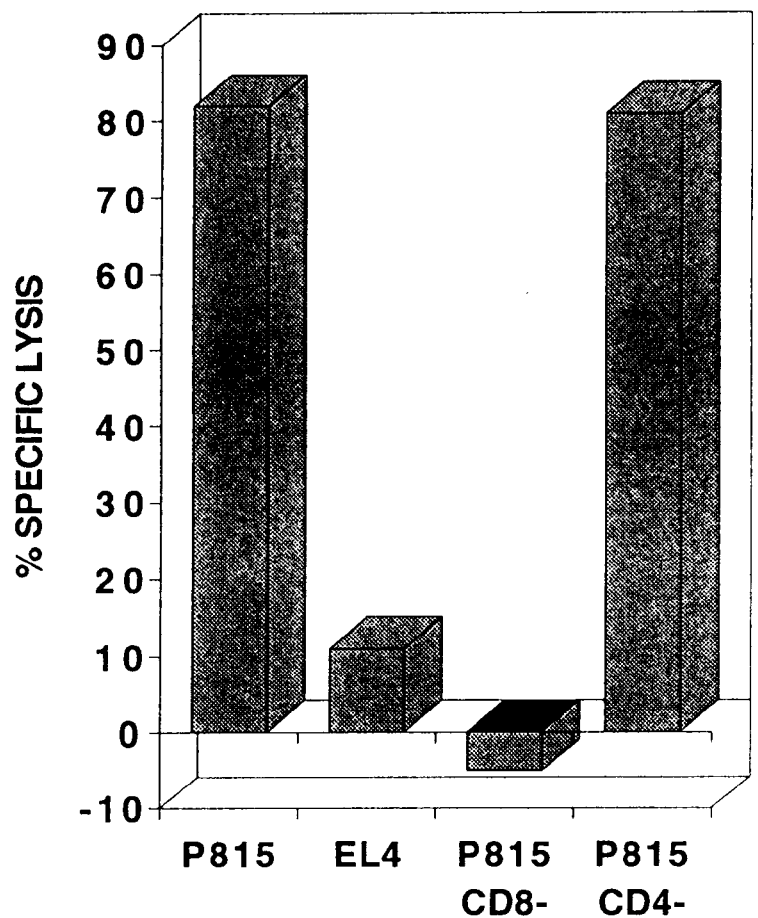
FIG. 5 is a graph that shows that immunization of mice with pDIP/PyCSP.1 induces MHC restricted, CD8+ T cell-dependent CTL against PyCSP.

FIG. 5 is a graph of induction of MHC restricted, CD8+ T cell-dependent CTL against PyCSP by immunization with pDIP/PyCSP.1. Two weeks after the second dose of pDIP/PyCSP.1, mice were euthanized and spleen cells isolated, stimulated in vitro for 5 days with peptide PyCSP (281–296; SYVPSAEQILEFVKQI), and then assessed for cytolytic activity as previously described[21]. At an effector to target ratio of 60:1 T cells lysed MHC matched P815 cells (H-2d) pulsed with the same PyCSP(281–296) peptide, but did not lyse peptide-pulsed EL-4 cells (H-2b). This cytolytic activity was eliminated by depletion of CD8+ T cells, but unaffected by depletion of CD4+ T cells. These sera also inhibited sporozoite invasion and development within primary mouse hepatocytes in vitro[33]. Hepatocytes isolated from Balb/C mice were seeded in 8-chamber Lab-Tek plastic slides at $1 \times 10^5$ cells/chamber. After 24 h of incubation at 37° C. in an atmosphere of 5% $CO_2$ in air, medium was removed and $5 \times 10^4$ salivary gland dissected sporozoites suspended in 25 µl of medium, and 25 µl of diluted sera from immunized or control mice added. After 3 hours incubation cultures were washed to remove unattached sporozoites and fresh medium was added. At 24 hours medium was changed and at 48 hours cultures were fixed and incubated with a Mab directed against liver stage parasites of P. yoelii (NYLSI) before incubating with FITC-labelled goat anti-mouse Ig. The number of liver-stage schizonts in triplicate cultures was counted using an Olympus fluorescence microscope. A 1:10 dilution of serum from a mouse immunized with 3 doses of vaccine, serum with an IFAT titer against sporozoites of 20,480, inhibited sporozoite invasion and development by 80±5% as compared to serum from a mouse immunized with plasmid control (9.3±2.5 schizonts per well vs 46.0±3.6 schizonts/well, p=0.001, Student's t test, 2-tailed). Sera from mice immunized with irradiated *P. yoelii* sporozoites do not inhibit sporozoite invasion and development in this assay[33].

Since CD8+ CTL against the PyCSP have been shown to adoptively transfer protection[16], and CD8+ T cells are required for the protection against *P. yoelii* induced by immunization with irradiated sporozoites[34], recombinant P815 mastocytoma cells expressing PyCSP[30], or recombinant viruses expressing PyCSP[22], we wanted to determine if immunization with the PyCSP plasmid, pDIP/PyCSP.1, induced CTL. The results indicate that immunization with pDIP/PyCSP.1 induces MHC restricted, CD8+ T cell-dependent cytolytic activity (FIG. 5). Furthermore, the cytolytic activity is significantly greater than that found after immunization with irradiated sporozoites (FIG. 6A, B).

Before achieving consistency of induction of antibodies by modifying injection techniques, we tested 2 immunized mice without antibodies to sporozoites, and 4 immunized mice that had antibodies to sporozoites for CTL. All 4 of the mice with antibodies and none of the mice without antibodies had demonstrable CTL (data not shown). This suggests that when this vaccine induces immune responses, it induces antibodies and CTL.

Figure 6A:
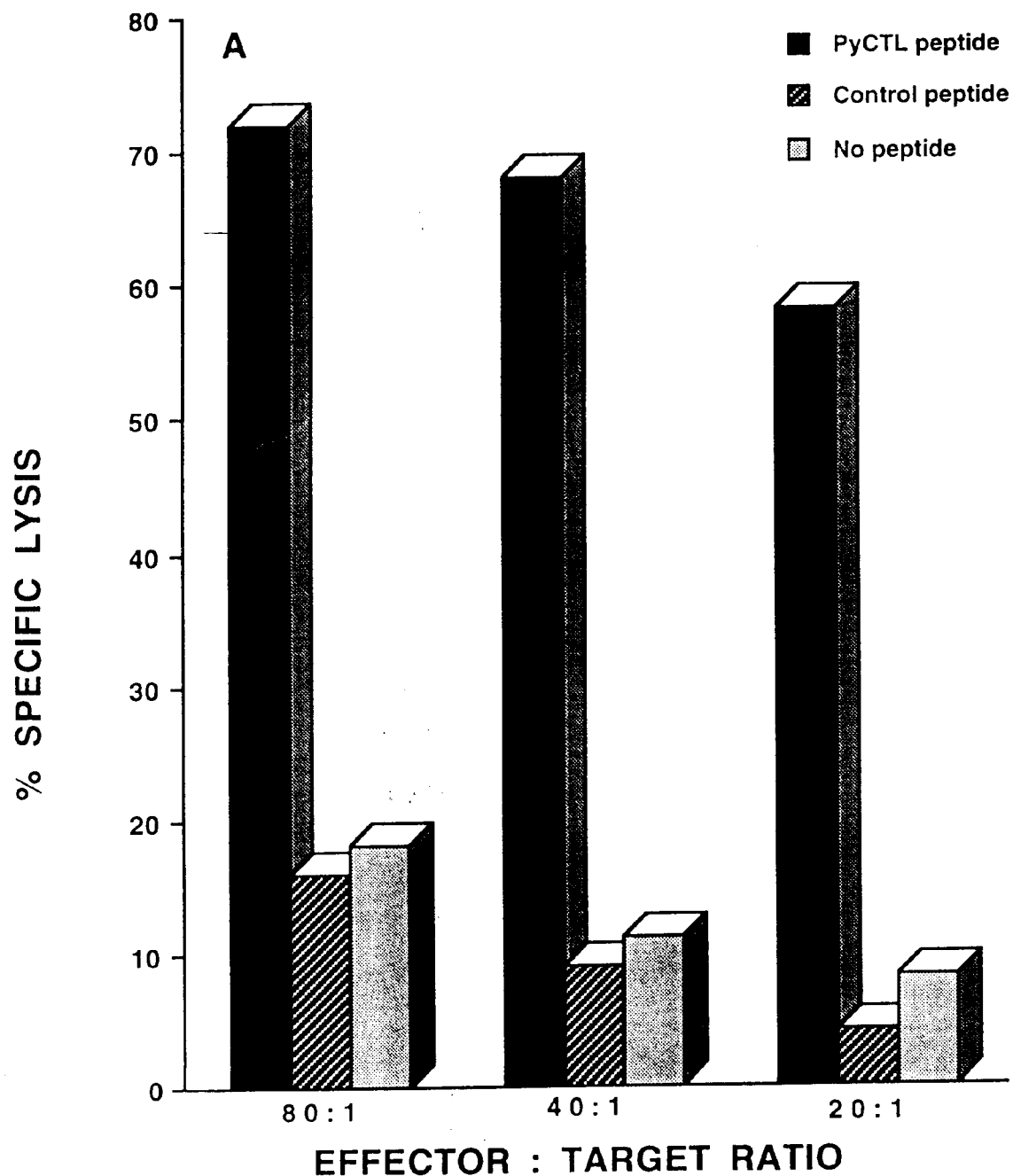
Figure 6B:
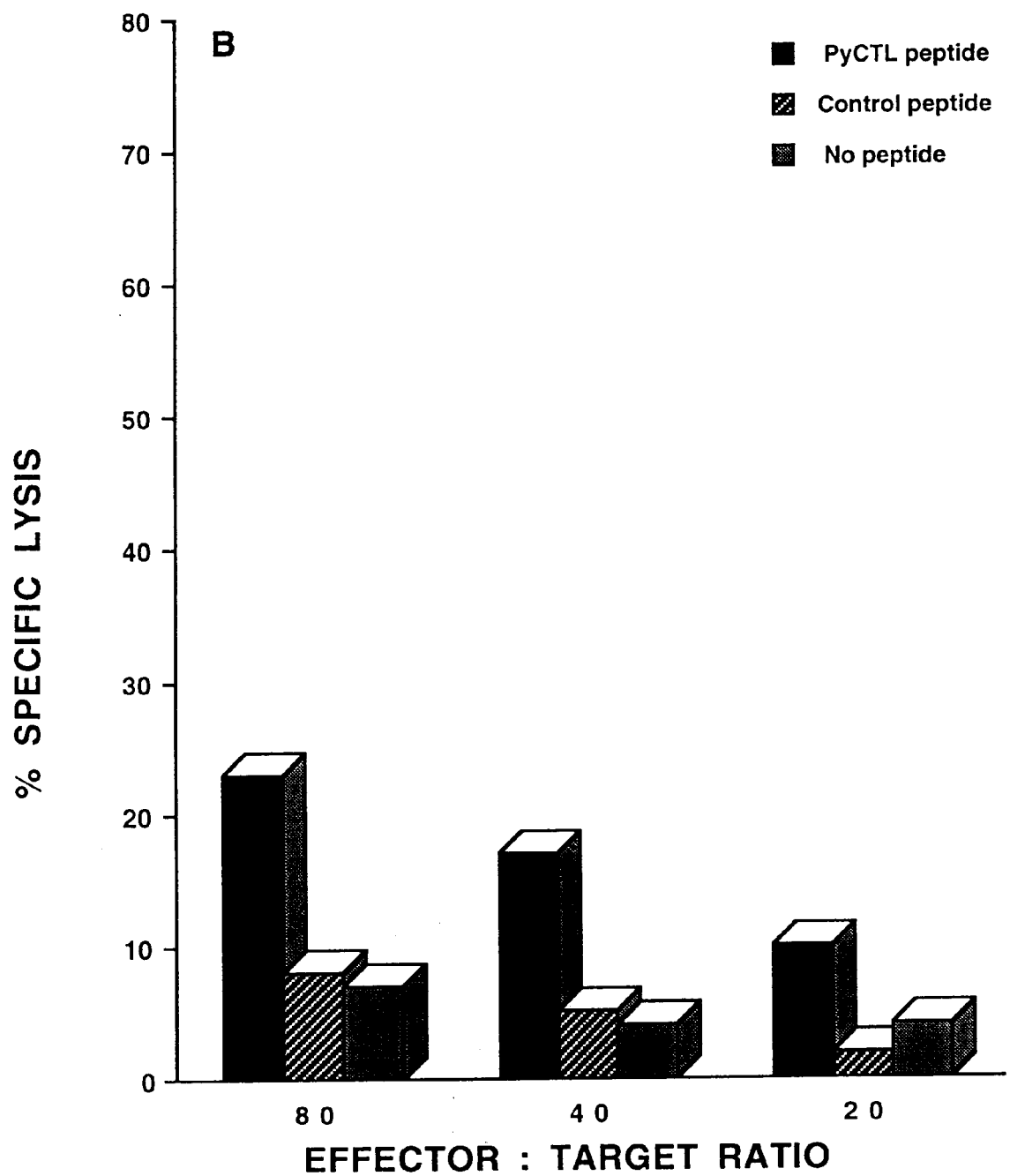

The data shown in FIGS. 6A & B were taken from a CTL assay performed 2 weeks after the last immunization as described for FIG. 5. Significantly more cytolytic activity was demonstrated at all effector to target ratios against P815 cells pulsed with the PyCSP (281–296) peptide using cells from mice immunized with pDIP/PyCSP.1. These effectors did not lyse targets pulsed with a peptide from the *P. falciparum* CSP, PfCSP (368–390) that includes a CTL epitope and did not lyse P815 cells that had not been exposed to peptide (FIG. 6A & 6B). Spleen cells from naive mice and mice immunized with the plasmid control, and stimulated in vitro with peptide PyCSP (281–296), had no greater activity against P815 cells targets pulsed with PyCSP (281–296) peptide than against targets pulsed with the PfCSP (368–390) control peptide or targets not exposed to peptide (data not shown).

EXAMPLE 2

Having established that immunization with pDIP/PyCSP.1 induced biologically active antibodies and CTL against the PyCSP, we asked if immunization with the vaccine would reduce liver stage infections. Groups of mice were immunized with 3 doses of pDIP/PyCSP.1 or control plasmid at 3 week intervals. Two weeks after the third dose 3 immunized mice with highest IFAT titers (20,480), and 3 controls were selected for IV challenge with $5 \times 10^5$ *P. yoelii* sporozoites. Since the $ID_{50}$ for *P. yoelii* sporozoites is often less than 2 sporozoites[30], this is an enormous challenge representing greater than $10^5$ $ID_{50}$s. Forty-two hours after IV inoculation of $5 \times 10^5$ sporozoites into immune or control mice, mice were euthanized. Livers were removed and used to prepare single cell suspensions of hepatocytes in medium. After cells were counted, $2 \times 10^5$ hepatocytes were distributed into 10 wells of a multi-well slide. Slides were dried and frozen at −70° C. until studied.

To count the number of schizonts, slides were dried and incubated with NYLS1 before incubating with FITC-labelled goat anti-mouse Ig. The numbers of liver-stage schizonts in each well of coded slides were counted blindly by fluorescence microscopy. 70 wells containing a total of $1.4 \times 10^6$ hepatocytes were read per liver. There was an 85.6±4.0% reduction in the number of liver stage schizonts in the group that received pDIP/PyCSP.1 as compared to the mice that received the plasmid without the PyCSP insert (12.7±3.5 schizonts/$1.4 \times 10^6$ hepatocytes vs 88.0±17.8 schizonts/$1.4 \times 10^6$ hepatocytes, p=0.002, Student's t test, 2-tailed). Having demonstrated that immunization with this vaccine significantly reduced the numbers of infected hepatocytes, we asked if it could protect against blood stage infection. The results of an initial experiment clearly demonstrate that it can (Table 2), and indicate that the protection is comparable to that induced by immunization with recombinant P815 cells expressing PyCSP[30].

TABLE 2

Protection against sporozoite challenge. Mice were immunized with pDIP/PyCSP.1 at 0 and 8 weeks, and challenged 2 weeks later by IV injection of 100 *P. yoelii* sporozoites. Plasmid controls received the pBC12/CMV/IL-2 plasmid without the PyCSP insert, and naive controls were not immunized. Protection was defined as absence of *P. yoelii* parasites on blood smears obtained on days 4, 7, 8, 9, 11 and 14 after infection.

| Mouse | IFAT Titer at Challenge | Protection |
| --- | --- | --- |
| 1A | 20,480 | yes |
| 2A | 20,480 | yes |
| 5A | 10,240 | no |
| plasmid controls (n = 3) | <10 | no |
| naive controls (n = 7) | <10 | no |

EXAMPLE 3 pDIP/PyCSP.1 is modified to remove the gene encoding PyCSP and DNA encoding influenza A nucleoprotein is inserted to form, pDIP/infNP.1. After appropriate production and purification, mice are injected intramuscularly with 3 doses of 200 mcg of this plasmid DNA at 4 week intervals. Four weeks after the third dose, specimens from the mice are assessed for specific antibody and cellular immune responses against influenza A nucleoprotein, and the mice are challenged by intranasal administration of $10^{2.5}$ $TCID_{50}$ (mean tissue culture infectious dose) of influenza A virus. After establishing the efficacy in mice, large numbers of humans are immunized in a double blind placebo controlled field trial.

EXAMPLE 4 pDIP/PyCSP.1 is modified to remove nucleotides 1383 to 2155 of the PyCSP and the gene encoding influenza A nucleoprotein is inserted to form, pDIP/CS-infNP.1. After appropriate production and purification, mice are injected intramuscularly with 3 doses of 200 mcg of this plasmid DNA at 4 week intervals. Four weeks after the third dose, specimens from the mice are assessed for specific antibody and cellular immune responses against influenza nucleoprotein, and the mice are challenged by intranasal administration of $10^{2.5}$ $TCID_{50}$ (mean tissue culture infectious dose) of influenza A virus. After establishing the efficacy in mice, large numbers of humans are immunized in a double blind placebo controlled field trial.

EXAMPLE 5 pDIP/PyCSP.1 is modified to remove the PyCSP gene and the gene encoding outer surface protein (OSP-A) of *Borrelia burgdorferi* (a candidate Lyme disease vaccine) is inserted to form, pDIP/BbOSPA.1. After appropriate production and purification, mice are injected intramuscularly with 3 doses of 200 mcg of this plasmid DNA at 4 week intervals. Four weeks after the third dose, specimens from the mice are assessed for specific antibody and cellular immune responses against recombinant purified OSP-A. After establishing the safety and immunogenicity of this vaccine in mice, human volunteers chosen from a population of individuals at high risk of contracting Lyme disease are immunized in a double blind placebo controlled study.

EXAMPLE 6 pDIP/PyCSP.1 is modified to remove the nucleotides 1383 to 2155 of the PyCSP and the gene encoding the outer surface protein (OSP-A) of *Borrelia burgdorferi* (a candidate Lyme disease vaccine) is inserted to form, pDIP/CS-BbOSPA.1. After appropriate production and purification, mice are injected intramuscularly with 3 doses of 200 mcg of this plasmid DNA at 4 week intervals. Four weeks after the third dose, specimens from the mice are assessed for specific antibody and cellular immune responses against purified recombinant OSP-A. After establishing the safety and immunogenicity of this vaccine in mice, human volunteers chosen from a population of individuals at high risk of contracting Lyme disease are immunized in a double blind placebo controlled study.

EXAMPLE 7 pDIP/PyCSP.1 is modified to remove the PyCSP gene and the gene encoding HIS-62 (a protective antigen) from *Histoplasma capsulatum* is inserted to form, pDIP/HIS62.1. After appropriate production and purification, mice are injected intramuscularly with 3 doses of 200 mcg of this plasmid DNA at 4 week intervals. Four weeks after the third dose, specimens from the mice are assessed for specific antibody and cellular immune responses against purified recombinant HIS-62. After establishing the safety and immunogenicity of this vaccine in mice, human volunteers chosen from a population of individuals at high risk of contracting histoplasmosis are immunized in a double blind placebo controlled study.

EXAMPLE 8 pDIP/PyCSP.1 is modified to remove nucleotides 1383 to 2155 of the PyCSP and the gene encoding HIS-62 (a protective antigen) from *Histoplasma capsulatum* is inserted to form, pDIP/CS-HIS62.1. After appropriate production and purification, mice are injected intramuscularly with 3 doses of 200 mcg of this plasmid DNA at 4 week intervals. Four weeks after the third dose, specimens from the mice are assessed for specific antibody and cellular immune responses against HIS-62. After establishing the safety and immunogenicity of this vaccine in mice, human volunteers chosen from a population of individuals at high risk of contracting histoplasmosis are immunized are immunized in a double blind placebo controlled trial.

EXAMPLE 9 pDIP/PyCSP.1 is modified to remove the PyCSP gene and DNA encoding tetanus toxin is inserted to form, pDIP/tet.1. After appropriate production and purification, mice are injected intramuscularly with 3 doses of 200 mcg of this plasmid DNA at 4 week intervals. Four weeks after the third dose, specimens from the mice are assessed for specific antibody and cellular immune responses against tetanus toxin. After establishing the safety and immunogenicity of this vaccine in mice, human volunteers are immunized in a double blind placebo controlled trial comparing pDIP/tet.1 to standard tetanus toxoid vaccine for their capacities to induce antibodies and T cell proliferative responses against tetanus toxin.

EXAMPLE 10 pDIP/PyCSP.1 is modified to remove nucleotides 1383 to 2155 of the PyCSP and the gene encoding tetanus toxin is inserted to form, pDIP/CS-tet.1. After appropriate production and purification, mice are injected intramuscularly with 3 doses of 200 mcg of this plasmid DNA at 4 week intervals. Four weeks after the third dose, specimens from the mice are assessed for specific antibody and cellular immune responses against tetanus toxin. After establishing the safety and immunogenicity of this vaccine in mice, human volunteers are immunized in a double blind placebo controlled trial comparing pDIP/CS-tet.1 to standard tetanus toxoid vaccine for their capacities to induce antibodies and T cell proliferative responses against tetanus toxin.

EXAMPLE 11 pDIP/PyCSP.1 is modified to remove the PyCSP gene and the gene encoding the *P. falciparum* CSP inserted to form, pDIP/PfCSP.1. After appropriate production and purification, mice are injected intramuscularly with 3 doses of 200 mcg of this plasmid DNA at 4 week intervals. Four weeks after the third dose, specimens from the mice are assessed for antibodies to the PfCSP, T cell proliferative responses to PfCSP, and CTL against PfCSP. After establishing the safety and immunogenicity of this vaccine in mice, human volunteers are immunized with pDIP/PfCSP.1 in a double blind placebo controlled trial.

EXAMPLE 12 pDIP/PyCSP.1 is modified to remove nucleotides 1383 to 2155 of the PyCSP and the gene encoding the *P. falciparum* CSP inserted to form, pDIP/CS-PfCSP.1. After appropriate production and purification, mice are injected intramuscularly with 3 doses of 200 mcg of this plasmid DNA at 4 week intervals. Four weeks after the third dose, specimens from the mice are assessed for antibodies to the PfCSP, T cell proliferative responses to PfCSP, and CTL against PfCSP. After establishing the safety and immunogenicity of this vaccine in mice, human volunteers are immunized with pDIP/CS-PfCSP.1 in a double blind placebo controlled trial.

EXAMPLE 13

Any polynucleotide delivery vector (PDV) designed for in vivo use (injection, inhalation, topical application, ingestion) is modified and the gene encoding the *P. falciparum* CSP inserted to form, pPDV/PfCSP.1 (a double stranded DNA plasmid in this example but not limited to plasmid vectors only). After appropriate production and purification, mice are injected intramuscularly with 3 doses of 200 mcg of this plasmid DNA at 4 week intervals. Four weeks after the third dose, specimens from the mice are assessed for antibodies to the PfCSP, T cell proliferative responses to PfCSP, and CTL against PfCSP. After establishing the safety and immunogenicity of this vaccine in mice, human volunteers are immunized with pPDV/PfCSP.1 in a double blind placebo controlled trial. Polynucleotide vaccines provide an entirely new approach to developing multi-component vaccines against the microorganisms that cause malaria without the often difficult, time-consuming, and expensive requirement for production, purification, and mixing of synthetic peptides, purified recombinant proteins, recombinant live vectors, and adjuvants; processes that have greatly impeded the development of truly effective malaria vaccines as described in the Institute of Medicine report (page 3, line 10 to page 8, line 20, quoted above).

Obviously, many modifications and variations of the present invention are possible in light of the above teachings. It is therefore to be understood that, within the scope of the appended claims, the invention may be practiced otherwise than as specifically described.

References

1. Institute of Medicine. Malaria: Obstacles and Opportunities. S. C. Oaks, V. S. Mitchell, G. W. Pearson and C. Carpenter, eds. National Academy Press, Washington D.C. (1991).
2. H. W. Mulligan, P. Russell and B. N. Mohan. *J. Mal. Inst. India.* 4: 25 (1941).
3. R. S. Nussenzweig, J. Vanderberg, H. Most and C. Orton. *Nature* 216: 160 (1967).
4. D. F. Clyde, V. C. McCarthy, R. M. Miller and R. B. Hornick. *Am. J. Med. Sci.* 266: 398 (1973).
5. D. F. Clyde, V. C. McCarthy, R. M. Miller and W. E. Woodward. *Am. J. Trop. Med. Hyg.* 24: 397 (1975).
6. D. F. Clyde, H. Most, V. C. McCarthy and J. P. Vanderberg. *Am. J. Med. Sci.* 266: 169 (1973).
7. K. H. Rieckmann et al., *Trans. R. Soc. Trop. Med. Hyg.* 68: 258 (1974).
8. K. H. Rieckmann, R. L Beaudoin, J. S. Cassells and D. W. Sell. *Bull. W.H.O.* 57: 261 (1979).
9. D. Herrington et al., *Am. J. Trop. Med. Hyg.* 45: 539 (1991).
10. J. E. Egan et al., *Am. J. Trop. Med. Hyg.* (1992) (In Press).
11. R. Edelman et al.. *J. Infect. Dis.* 168: 1066 (1993).
12. N. H. Fairley. *Trans. Roy. Soc. Trop. Med. Hyg* 40: 621 (1947).
13. S. L. Hoffman, V. Nussenzweig, J. C. Sadoff and R. Nussenzweig. *Science* 252: 520 (1991).
14. Y. Charoenvit et al., *J. Immunol.* 146: 1020 (1991).
15. M. M. Rodrigues et al., *Int. Immunol.* 3: 579 (1991).
16. W. R. Weiss et al., *J. Immunol.* 149: 2103 (1992).
17. L. Renia et al., ibid. 150: 1471 (1993).
18. A. A. Lal et al., *Proc. Natl. Acad. Sci. U.S.A.* 84: 8647 (1987).
19. M. Sedegah et al. in Technological Advances in Vaccine Development, L. Lasky, Ed. (Alan R. Liss Inc., New York, 1988), pp. 295–309.
20. M. Sedegah et al., *Bull. World Health Organ.* 68 (suppl.) 109 (1990).
21. M. Sedegah et al,. *Vaccine* 10: 578 (1992).
22. S. Li et al., *Proc. Natl. Acad. Sci. U.S.A.* 90: 5214 (1993).
23. D. Tang, M. DeVit and S. A. Johnston. *Nature* 356: 152 (1992).
24. B. Wang et al., *Proc. Natl. Acad. Sci. U.S.A.* 90: 4156 (1993).
25. G. J. M. Cox et al., *J. of Virology* 67: 5664 (1993).
26. J. B. Ulmer et al., ibid. 259: 1745 (1993).
27. B. R. Cullen. *Cell* 46: 973 (1986).
28. R. C. Hedstrom et al., *Bull. World Health Organ.* 68 (suppl.) 152 (1990).
29. W. O. Rogers, M. D. Rogers, R. C. Hedstrom and S. L. Hoffman. *Mol. Biochem. Parasitol.* 53: 45 (1992).
30. S. Khusmith et al., *Science* 252: 715 (1991).
31. A. A. Lal, V. F. de la Cruz and J. A. Welsh. *J. Biol. Chem.* 262: 2937 (1987).
32. A. Wortman et al., *Microb. Pathog.* 6: 227 (1989).
33. S. Mellouk et al., *Bull. World Health Organ.* 68 (suppl.) 52 (1990).
34. W. R. Weiss et al., *Proc. Natl. Acad. Sci U.S.A.* 85: 573 (1988).

What is claimed is:

1. A method of controlling malaria in mammals comprising injecting a polynucleotide delivery vector into a mammal, wherein said vector comprises at least one DNA sequence encoding a Plasmodium species protein operably linked to a mammalian specific promoter, wherein expression of said DNA sequence results in the production of an immune response to the malaria protein and a reduction in malaria parasites at the pre-erythrocytic, erythrocytic, and gametocyte stages of infection.

2. The method according to claim 1 wherein the Plasmodium species is *P. falciparum.*

3. The method according to claim 1 wherein the Plasmodium species is *P. vivax.*

4. The method according to claim 1 wherein the Plasmodium species is *P. yoelii.*

5. A pharmaceutical composition comprising a polynucleotide delivery vector comprising a DNA sequence encoding at least one Plasmodium species protein operably linked to a mammalian specific promoter and a pharmaceutical carrier.

6. The pharmaceutical composition according to claim 5 wherein the Plasmodium species is *P. falciparum.*

7. The pharmaceutical composition according to claim 5 wherein the Plasmodium species is *P. vivax.*

8. The pharmaceutical composition according to claim 5 wherein the Plasmodium species is *P. yoelii.*

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 5552 base pairs
      (B) TYPE: nucleic acid
      (C) STRANDEDNESS: double
      (D) TOPOLOGY: circular (iii) HYPOTHETICAL: NO (iv) ANTI-SENSE: NO (ix) FEATURE:
      (A) NAME/KEY: promoter
      (B) LOCATION: 1..755
      (C) IDENTIFICATION METHOD: experimental
      (D) OTHER INFORMATION: /function= "promoter"
          /evidence= EXPERIMENTAL
          /label= CMV-IE
          /note= "This feature acts as a promoter for any downstream DNA sequence."
          /citation= ([2])

(ix) FEATURE:
      (A) NAME/KEY: CDS
      (B) LOCATION: 933..2367
      (C) IDENTIFICATION METHOD: experimental
      (D) OTHER INFORMATION: /codon_start= 933
          /function= "protein protective against malaria"

```
            /product= "protein"
            /evidence= EXPERIMENTAL
            /number= 1
            /label= IL2-CSP
            /citation= ([1])

(x) PUBLICATION INFORMATION:
         (A) AUTHORS: Sedegah, Martha
                     Hedstrom, Richard C.
                     Hoffman, Stephen L.
         (B) TITLE: Vaccination with Plasmodium yoelii CS protein
                    plasmid DNA protects against malaria
         (C) JOURNAL: Science (x) PUBLICATION INFORMATION:
         (A) AUTHORS: Cullen, Bryan R.
         (B) TITLE: TRANS-ACTIVATION OF HUMAN IMMUNODEFICIENCY
                    VIRUS OCCURS VIA A BIMODAL MECHANISM
         (C) JOURNAL: CELL
         (D) VOLUME: 46
         (F) PAGES: 973-982
         (G) DATE: 26 SEP-1986
         (K) RELEVANT RESIDUES IN SEQ ID NO:1: FROM 1 TO 4732

(xi) SEQUENCE DESCRIPTION: SEQ ID NO:1:
```

```
AGCTTCCCAT TGCATACGTT GTATCCATAT CATAATATGT ACATTTATAT TGGCTCATGT      60

CCAACATTAC CGCCATGTTG ACATGGATTA TTGACTAGTT ATTAATAGTA ATCAATTACG     120

GGGTCATTAG TTCATAGCCC ATATATGGAG TTCCGCGTTA CATAACTTAC GGTAAATGGC     180

CCGCCTGGCT GACCGCCCAA CGACCCCCGC CCATTGACGT CAATAATGAC GTATGTTCCC     240

ATAGTAACGC CAATAGGGAC TTTCCATTGA CGTCAATGGG TGGAGTATTT ACGGTAAACT     300

GCCCACTTGG CAGTACATCA AGTGTATCAT ATGCCAAGTA CGCCCCCTAT TGACGTCAAT     360

GACGGTAAAT GGCCCGCCTG GCATTATGCC CAGTACATGA CCTTATGGGA CTTTCCTACT     420

TGGCAGTACA TCTACGTATT AGTCATCGCT ATTACCATGG TGATGCGGTT TTGGCAGTAC     480

ATCAATGGGC GTGGATAGCG GTTTGACTCA CGGGGATTTC CAAGTCTCCA CCCCATTGAC     540

GTCAATGGGA GTTTGTTTTG GCACCAAAAT CAACGGGACT TTCCAAAATG TCGTAACAAC     600

TCCGCCCCAT TGACGCAAAT GGGCGGTAGG CGTGTACGGT GGGAGGTCTA TATAAGCAGA     660

GCTCGTTTAG TGAACCGCCA GATCGCCTGG AGACGCCATC CACGCTGTTT TGACCTCCAT     720

AGAAGACACC GGGACCGATC CAGCCTCCCC TCGAAGCTTG GTAAGTGACC AGCTACAGTC     780

GGAAACCATC AGCAAGCAGG TATGTACTCT CCAGGGTGGG CCTGGCTTCC CCAGTCAAGA     840

CTCCAGGGAT TGAGGGACG CTGTGGGCTC TTCTCTTACA TGTACCTTTT GCTAGCCTCA     900

ACCCTGACTA TCTTCCAGGT CATTGTTCCA AC ATG GCC CTG TGG ATC GAC AGG      953
                                  Met Ala Leu Trp Ile Asp Arg
                                   1               5

ATG CAA CTC CTG TCT TGC ATT GCA CTA AGT CTT GCA CTT GTC ACA AAC     1001
Met Gln Leu Leu Ser Cys Ile Ala Leu Ser Leu Ala Leu Val Thr Asn
         10                  15                  20

AGT GCA CCT ACT TCA AGT TCT ACA AAG AAA ACA CAG CTA CAA CTG GAG     1049
Ser Ala Pro Thr Ser Ser Ser Thr Lys Lys Thr Gln Leu Gln Leu Glu
     25                  30                  35

CAT TTA CTG CTG GAT TTA CAG ATG ATT TTG AAT GGA ATT AAT AAT TAC     1097
His Leu Leu Leu Asp Leu Gln Met Ile Leu Asn Gly Ile Asn Asn Tyr
 40                  45                  50                  55

AAG AAT CCC AAA CTC ACC AGG ATG CTC ACA TTT AAG TTT TAC ATG CCC     1145
Lys Asn Pro Lys Leu Thr Arg Met Leu Thr Phe Lys Phe Tyr Met Pro
             60                  65                  70

AAG AAG GCC ACA GAA CTG AAA CAT CTT CAG TGT CTA GAG GAT CCC AAA     1193
Lys Lys Ala Thr Glu Leu Lys His Leu Gln Cys Leu Glu Asp Pro Lys
             75                  80                  85
```

-continued

```
ATG AAG AAG TGT ACC ATT TTA GTT GTA GCG TCA CTT TTA TTA GTT GAT     1241
Met Lys Lys Cys Thr Ile Leu Val Val Ala Ser Leu Leu Leu Val Asp
         90                  95                 100

TCT CTA CTT CCA GGA TAT GGA CAA AAT AAA AGT GTC CAA GCC CAA AGA     1289
Ser Leu Leu Pro Gly Tyr Gly Gln Asn Lys Ser Val Gln Ala Gln Arg
    105                 110                 115

AAC TTA AAC GAG CTA TGT TAC AAT GAA GAA AAT GAT AAT AAA TTG TAT     1337
Asn Leu Asn Glu Leu Cys Tyr Asn Glu Glu Asn Asp Asn Lys Leu Tyr
120                 125                 130                 135

CAC GTC CTT AAC TCG AAG AAT GGA AAA ATA TAC AAT CGA AAT ATA GTC     1385
His Val Leu Asn Ser Lys Asn Gly Lys Ile Tyr Asn Arg Asn Ile Val
                140                 145                 150

AAC AGA TTA CTT GGC GAT GCT CTC AAC GGA AAA CCA GAA GAA AAA AAA     1433
Asn Arg Leu Leu Gly Asp Ala Leu Asn Gly Lys Pro Glu Glu Lys Lys
            155                 160                 165

GAT GAT CCC CCA AAA GAT GGC AAC AAA GAT GAT CTT CCA AAA GAA GAA     1481
Asp Asp Pro Pro Lys Asp Gly Asn Lys Asp Asp Leu Pro Lys Glu Glu
        170                 175                 180

AAA AAA GAT GAT CTT CCA AAA GAA GAA AAA AAA GAT GAT CCC CCA AAA     1529
Lys Lys Asp Asp Leu Pro Lys Glu Glu Lys Lys Asp Asp Pro Pro Lys
    185                 190                 195

GAT CCT AAA AAA GAT GAT CCA CCA AAA GAG GCT CAA AAT AAA TTG AAT     1577
Asp Pro Lys Lys Asp Asp Pro Pro Lys Glu Ala Gln Asn Lys Leu Asn
200                 205                 210                 215

CAA CCA GTA GTG GCA GAT GAA AAT GTA GAT CAA GGG CCA GGA GCA CCA     1625
Gln Pro Val Val Ala Asp Glu Asn Val Asp Gln Gly Pro Gly Ala Pro
                220                 225                 230

CAA GGG CCA GGA GCA CCA CAA GGG CCA GGA GCA CCA CAG GGG CCA GGA     1673
Gln Gly Pro Gly Ala Pro Gln Gly Pro Gly Ala Pro Gln Gly Pro Gly
            235                 240                 245

GCA CCA CAG GGG CCA GGA GCA CCA CAA GGG CCA GGA GCA CCA CAA GGA     1721
Ala Pro Gln Gly Pro Gly Ala Pro Gln Gly Pro Gly Ala Pro Gln Gly
        250                 255                 260

CCA GGA GCA CCA CAA GGG CCA GGA GCA CCA CAA GGG CCA GGA GCA CCA     1769
Pro Gly Ala Pro Gln Gly Pro Gly Ala Pro Gln Gly Pro Gly Ala Pro
    265                 270                 275

CAA GGG CCA GGA GCA CCA CAG GGG CCA GGA GCA CCA CAA GGG CCA GGA     1817
Gln Gly Pro Gly Ala Pro Gln Gly Pro Gly Ala Pro Gln Gly Pro Gly
280                 285                 290                 295

GCA CCA CAA GGA CCA GGA GCA CCA CAG GGT CCA GGA GCA CCA CAA GGA     1865
Ala Pro Gln Gly Pro Gly Ala Pro Gln Gly Pro Gly Ala Pro Gln Gly
                300                 305                 310

CCA GGA GCA CCA CAA GGA CCA GGA GCA CCA CAA GGT CCA GGA GCA CCA     1913
Pro Gly Ala Pro Gln Gly Pro Gly Ala Pro Gln Gly Pro Gly Ala Pro
            315                 320                 325

CAG GGG CCA GGA GCA CCA CAA GGG CCA GGA GCA CCA CAA GAA CCA CCC     1961
Gln Gly Pro Gly Ala Pro Gln Gly Pro Gly Ala Pro Gln Glu Pro Pro
        330                 335                 340

CAA CAA CCA CCC CAA CAA CCA CCA CAA CAG CCA CCA CAA CAG CCA CCA     2009
Gln Gln Pro Pro Gln Gln Pro Pro Gln Gln Pro Pro Gln Gln Pro Pro
    345                 350                 355

CAA CAG CCA CCA CAA CAG CCA CCA CAA CAA CCA CGC CCA CAG CCA GAT     2057
Gln Gln Pro Pro Gln Gln Pro Pro Gln Gln Pro Arg Pro Gln Pro Asp
360                 365                 370                 375

GGT AAT AAC AAC AAT AAC AAT AAT AAT GGT AAT AAT AAT GAA GAT TCT     2105
Gly Asn Asn Asn Asn Asn Asn Asn Asn Gly Asn Asn Asn Glu Asp Ser
                380                 385                 390
```

```
TAT GTC CCA AGC GCG GAA CAA ATA CTA GAA TTT GTT AAA CAG ATA AGT    2153
Tyr Val Pro Ser Ala Glu Gln Ile Leu Glu Phe Val Lys Gln Ile Ser
            395                 400                 405

AGT CAA CTC ACA GAG GAA TGG TCT CAA TGT AGT GTA ACC TGT GGT TCT    2201
Ser Gln Leu Thr Glu Glu Trp Ser Gln Cys Ser Val Thr Cys Gly Ser
        410                 415                 420

GGT GTA AGA GTT AGA AAA CGA AAA AAT GTA AAC AAG CAA CCA GAA AAT    2249
Gly Val Arg Val Arg Lys Arg Lys Asn Val Asn Lys Gln Pro Glu Asn
    425                 430                 435

TTG ACC TTA GAG GAT ATT GAT ACT GAA ATT TGT AAA ATG GAT AAA TGT    2297
Leu Thr Leu Glu Asp Ile Asp Thr Glu Ile Cys Lys Met Asp Lys Cys
440                 445                 450                 455

TCA AGT ATA TTT AAT ATT GTA AGC AAT TCA TTA GGA TTT GTA ATA TTA    2345
Ser Ser Ile Phe Asn Ile Val Ser Asn Ser Leu Gly Phe Val Ile Leu
                460                 465                 470

TTA GTA TTA GTA TTC TTT AAT T AAATAAACAT TACACATTAT TATAAATATT     2397
Leu Val Leu Val Phe Phe Asn
            475

TATATATTAT ATAAATATTT TATATACATA TAATGTGTGT AGACTTTATT TTTTGTATTG   2457

TGAACTTTCC TCATTTATTA CGATTATTTT TATATATATA CATATTTAAT ATGTAAATTA   2517

AAAGAAAAAA GAAATAATAG AAATCTTATT ATATTTATGA TATAAATTAA AAAAATAAAA   2577

TATATATACA TTACAAAATT TACTTTTTTT AGTTTATTTT TTTCGTGTTT ATTATATATG   2637

TAATTAACTT GTTATGACGA TGGGTACCCA TTTGGGGACC CCATAGAGCA CCGCACCGAC   2697

CGAGGGATGG TAACAGGATG TGTAGGTTTT GGAGGCCCAT ATGTCCATTC ATGACCAGTG   2757

ACTTGTCTCA CAGCCATGCA ACCCTTGCCT CCTGTGCTGA CTTAGCAGGG GATAAAGTGA   2817

GAGAAAGCCT GGGCTAATCG GGGGTCGCT CGGCTCCTCC TAACTGGATT GTCCTATGTG    2877

TCTTTGCTTC TGTGCTGCTG ATGCTCTGCC CTGTGCTGAC ATGACCTCCC TGGCAGTGGC   2937

ACAACTGGAG CTGGGTGGAG GCCCGGGGGC CGGTGACCTT CAGACCTTGG CACTGGAGGT   2997

GGCCCGGCAG AAGCGCGGCA TCGTGGATCA GTGCTGCACC AGCATCTGCT CTCTCTACCA   3057

ACTGGAGAAC TACTGCAACT AGGCCCACCA CTACCCTGTC CACCCCTCTG CAATGAATAA   3117

AACCTTTGAA AGAGCACTAC AAGTTGTGTG TACATGCGTG CGTGTGCATA TGTGGTGCGG   3177

GGGGAACATG AGTGGGGTCG GCTGGAGTGG TCGCGGCTTA ATCTATCTGG CGATGATAAG   3237

CTGTCAAACA TGAGAATTCT TGAAGACGAA AGGGCCTCGT GATACGCCTA TTTTTATAGG   3297

TTAATGTCAT GATAATAATG GTTTCTTAGA CGTCAGGTGG CACTTTTCGG GGAAATGTGC   3357

GCGGAACCCC TATTTGTTTA TTTTTCTAAA TACATTCAAA TATGTATCCG CTCATGAGAC   3417

AATAACCCTG ATAAATGCTT CAATAATATT GAAAAAGGAA GAGTATGAGT ATTCAACATT   3477

TCCGTGTCGC CCTTATTCCC TTTTTTGCGG CATTTTGCCT TCCTGTTTTT GCTCACCCAG   3537

AAACGCTGGT GAAAGTAAAA GATGCTGAAG ATCAGTTGGG TGCACGAGTG GGTTACATCG   3597

AACTGGATCT CAACAGCGGT AAGATCCTTG AGAGTTTTCG CCCCGAAGAA CGTTTTCCAA   3657

TGATGAGCAC TTTTAAAGTT CTGCTATGTG GCGCGGTATT ATCCCGTGTT GACGCCGGGC   3717

AAGAGCAACT CGGTCGCCGC ATACACTATT CTCAGAATGA CTTGGTTGAG TACTCACCAG   3777

TCACAGAAAA GCATCTTACG GATGGCATGA CAGTAAGAGA ATTATGCAGT GCTGCCATAA   3837

CCATGAGTGA TAACACTGCG GCCAACTTAC TTCTGACAAC GATCGGAGGA CCGAAGGAGC   3897

TAACCGCTTT TTTGCACAAC ATGGGGGATC ATGTAACTCG CCTTGATCGT TGGGAACCGG   3957

AGCTGAATGA AGCCATACCA AACGACGAGC GTGACACCAC GATGCCTGCA GCAATGGCAA   4017

CAACGTTGCG CAAACTATTA ACTGGCGAAC TACTTACTCT AGCTTCCCGG CAACAATTAA   4077
```

```
TAGACTGGAT GGAGGCGGAT AAAGTTGCAG GACCACTTCT GCGCTCGGCC CTTCCGGCTG    4137

GCTGGTTTAT TGCTGATAAA TCTGGAGCCG GTGAGCGTGG GTCTCGCGGT ATCATTGCAG    4197

CACTGGGGCC AGATGGTAAG CCCTCCCGTA TCGTAGTTAT CTACACGACG GGGAGTCAGG    4257

CAACTATGGA TGAACGAAAT AGACAGATCG CTGAGATAGG TGCCTCACTG ATTAAGCATT    4317

GGTAACTGTC AGACCAAGTT TACTCATATA TACTTTAGAT TGATTTAAAA CTTCATTTTT    4377

AATTTAAAAG GATCTAGGTG AAGATCCGTA ATCTGCTGCT TGCAAACAAA AAACCACCG     4437

CTACCAGCGG TGGTTTGTTT GCCGGATCAA GAGCTACCAA CTCTTTTTCC GAAGGTAACT    4497

GGCTTCAGCA GAGCGCAGAT ACCAAATACT GTCCTTCTAG TGTAGCCGTA GTTAGGCCAC    4557

CACTTCAAGA ACTCTGTAGC ACCGCCTACA TACCTCGCTC TGCTAATCCT GTTACCAGTG    4617

GCTGCTGCCA GTGGCGATAA GTCGTGTCTT ACCGGGTTGG ACTCAAGACG ATAGTTACCG    4677

GATAAGGCGC AGCGGTCGGG CTGAACGGGG GGTTCGTGCA CACAGCCCAG CTTGGAGCGA    4737

ACGACCTACA CCGAACTGAG ATACCTACAG CGTGAGCATT GAGAAAGCGC CACGCTTCCC    4797

GAAGGGAGAA AGGCGGACAG GTATCCGGTA AGCGGCAGGG TCGGAACAGG AGAGCGCACG    4857

AGGGAGCTTC CAGGGGGAAA CGCCTGGTAT CTTTATAGTC CTGTCGGGTT TCGCCACCTC    4917

TGACTTGAGC GTCGATTTTT GTGATGCTCG TCAGGGGGGC GGAGCCTATG GAAAAACGCC    4977

AGCAACGTCG GGATGCGCCG CGTGCGGCTG CTGGAGATGG CGGACGCGAT GGATATGTTC    5037

TGCCAAGGGT TGGTTTGCGC ATTCACAGTT CTCCGCAAGA ATTGATTGGC TCCAATTCTT    5097

GGAGTGGTGA ATCCGTTAGC GAGGTGCCGC CGGCTTCCAT TCAGGTCGAG GTGGCCCGGC    5157

TCCATGCACC GCGACGCAAC GCGGGGAGGC AGACAAGGTA TAGGGCGGCG CCTACAATCC    5217

ATGCCAACCC GTTCCATGTG CTCGCCGAGG CGGCATAAAT CGCCGTGACG ATCAGCGGTC    5277

CAGTGATCGA AGTTAGGCTG GTAAGAGCCG CGAGCGATCC TTGAAGCTGT CCCTGATGGT    5337

CGTCATCTAC CTGCCTGGAC AGCATGGCCT GCAACGCGGG CATCCCGATG CCGCCGGAAG    5397

CGAGAAGAAT CATAATGGGG AAGGCCATCC AGCCTCGCGT CGAGCTTTTT GCAAAAGCCT    5457

AGGCCTCCAA AAAAGCCTCC TCACTACTTC TGGAATAGCT CAGAGGCCGA GGCGGCCTCG    5517

GCCTCTGCAT AAATAAAAAA AATTAGTCAG CCATG                              5552
```

(2) INFORMATION FOR SEQ ID NO:2:

(i) SEQUENCE CHARACTERISTICS:
        (A) LENGTH: 478 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Leu Trp Ile Asp Arg Met Gln Leu Leu Ser Cys Ile Ala Leu
 1               5                  10                  15

Ser Leu Ala Leu Val Thr Asn Ser Ala Pro Thr Ser Ser Ser Thr Lys
                20                  25                  30

Lys Thr Gln Leu Gln Leu Glu His Leu Leu Leu Asp Leu Gln Met Ile
            35                  40                  45

Leu Asn Gly Ile Asn Asn Tyr Lys Asn Pro Lys Leu Thr Arg Met Leu
        50                  55                  60

Thr Phe Lys Phe Tyr Met Pro Lys Lys Ala Thr Glu Leu Lys His Leu
65                  70                  75                  80
```

-continued

```
Gln Cys Leu Glu Asp Pro Lys Met Lys Lys Cys Thr Ile Leu Val Val
                 85                  90                  95

Ala Ser Leu Leu Leu Val Asp Ser Leu Leu Pro Gly Tyr Gly Gln Asn
            100                 105                 110

Lys Ser Val Gln Ala Gln Arg Asn Leu Asn Glu Leu Cys Tyr Asn Glu
        115                 120                 125

Glu Asn Asp Asn Lys Leu Tyr His Val Leu Asn Ser Lys Asn Gly Lys
    130                 135                 140

Ile Tyr Asn Arg Asn Ile Val Asn Arg Leu Leu Gly Asp Ala Leu Asn
145                 150                 155                 160

Gly Lys Pro Glu Glu Lys Lys Asp Asp Pro Lys Asp Gly Asn Lys
                165                 170                 175

Asp Asp Leu Pro Lys Glu Lys Lys Asp Asp Leu Pro Lys Glu Glu
            180                 185                 190

Lys Lys Asp Asp Pro Pro Lys Asp Pro Lys Lys Asp Asp Pro Pro Lys
        195                 200                 205

Glu Ala Gln Asn Lys Leu Asn Gln Pro Val Val Ala Asp Glu Asn Val
    210                 215                 220

Asp Gln Gly Pro Gly Ala Pro Gln Gly Pro Gly Ala Pro Gln Gly Pro
225                 230                 235                 240

Gly Ala Pro Gln Gly Pro Gly Ala Pro Gln Gly Pro Gly Ala Pro Gln
                245                 250                 255

Gly Pro Gly Ala Pro Gln Gly Pro Gly Ala Pro Gln Gly Pro Gly Ala
            260                 265                 270

Pro Gln Gly Pro Gly Ala Pro Gln Gly Pro Gly Ala Pro Gln Gly Pro
        275                 280                 285

Gly Ala Pro Gln Gly Pro Gly Ala Pro Gln Gly Pro Gly Ala Pro Gln
    290                 295                 300

Gly Pro Gly Ala Pro Gln Gly Pro Gly Ala Pro Gln Gly Pro Gly Ala
305                 310                 315                 320

Pro Gln Gly Pro Gly Ala Pro Gln Gly Pro Gly Ala Pro Gln Gly Pro
                325                 330                 335

Gly Ala Pro Gln Glu Pro Pro Gln Gln Pro Pro Gln Gln Pro Pro Gln
            340                 345                 350

Gln Pro Pro Gln Gln Pro Pro Gln Gln Pro Pro Gln Gln Pro Pro Gln
        355                 360                 365

Gln Pro Arg Pro Gln Pro Asp Gly Asn Asn Asn Asn Asn Asn Asn
    370                 375                 380

Gly Asn Asn Asn Glu Asp Ser Tyr Val Pro Ser Ala Glu Gln Ile Leu
385                 390                 395                 400

Glu Phe Val Lys Gln Ile Ser Ser Gln Leu Thr Glu Glu Trp Ser Gln
                405                 410                 415

Cys Ser Val Thr Cys Gly Ser Gly Val Arg Val Arg Lys Arg Lys Asn
            420                 425                 430

Val Asn Lys Gln Pro Glu Asn Leu Thr Leu Glu Asp Ile Asp Thr Glu
        435                 440                 445

Ile Cys Lys Met Asp Lys Cys Ser Ser Ile Phe Asn Ile Val Ser Asn
    450                 455                 460

Ser Leu Gly Phe Val Ile Leu Leu Val Leu Val Phe Phe Asn
465                 470                 475
```